United States Patent
Miao

(10) Patent No.: US 12,414,777 B2
(45) Date of Patent: Sep. 16, 2025

(54) FETCHING ASSEMBLY AND RELEASING ASSEMBLY FOR ANASTOMOSIS CLAMP

(71) Applicant: JIANGSU VEDKANG MEDICAL SCIENCE & TECHNOLOGY CO., LTD., Jiangsu (CN)

(72) Inventor: Donglin Miao, Jiangsu (CN)

(73) Assignee: JIANGSU VEDKANG MEDICAL SCIENCE & TECHNOLOGY CO., LTD., Changzhou (CN)

( * ) Notice: Subject to any disclaimer, the term of this patent is extended or adjusted under 35 U.S.C. 154(b) by 531 days.

(21) Appl. No.: 17/806,600

(22) Filed: Jun. 13, 2022

(65) Prior Publication Data

US 2022/0304695 A1    Sep. 29, 2022

Related U.S. Application Data

(63) Continuation of application No. PCT/CN2022/071619, filed on Jan. 12, 2022.

(30) Foreign Application Priority Data

Jan. 28, 2021    (CN) .......................... 202110114886.2

(51) Int. Cl.
*A61B 17/128*    (2006.01)
*A61B 17/08*    (2006.01)
(Continued)

(52) U.S. Cl.
CPC ........ *A61B 17/1285* (2013.01); *A61B 17/083* (2013.01); *A61B 17/10* (2013.01);
(Continued)

(58) Field of Classification Search
CPC ......... A61B 17/10; A61B 17/11; A61B 17/08; A61B 17/083; A61B 17/122;
(Continued)

(56) References Cited

U.S. PATENT DOCUMENTS 8,784,436 B2 *    7/2014  Ho  ........................ A61B 17/10
                                                           606/142
9,295,470 B2 *    3/2016  Baur  ...................... A61B 18/14
(Continued)

FOREIGN PATENT DOCUMENTS

CN        2098175 A1     9/2009
CN        102458264      5/2012
(Continued)

OTHER PUBLICATIONS

Invitation pursuant to Rule 62a(1) EPC of EP Corresponding Application 22726379.5 issued on Jan. 4, 2024 from the EPO.
(Continued)

*Primary Examiner* — Tuan V Nguyen
(74) *Attorney, Agent, or Firm* — Grossman, Tucker, Perreault & Pfleger, PLLC

(57) ABSTRACT

A fetching assembly for an anastomosis clamp. The fetching assembly includes a fetching cap, a fetching hook and an anastomosis clamp. The fetching cap is configured to be mounted on a front end of an endoscope and has an outer diameter smaller than an inner diameter of the anastomosis clamp. The fetching hook is configured to pass through the fetching cap and hook onto the anastomosis clamp. When the fetching hook is pulled backward, the anastomosis clamp can be sleeved on an outer peripheral surface of the fetching cap to restore the closed anastomosis clamp.

12 Claims, 17 Drawing Sheets

(51) Int. Cl.
    *A61B 17/10*      (2006.01)
    *A61B 17/122*     (2006.01)
    *A61B 17/00*      (2006.01)
    *A61B 17/12*      (2006.01)

(52) U.S. Cl.
    CPC .. *A61B 17/122* (2013.01); *A61B 2017/00296* (2013.01); *A61B 2017/00907* (2013.01); *A61B 2017/12004* (2013.01)

(58) Field of Classification Search
    CPC .............. A61B 17/1227; A61B 17/128; A61B 17/1285; A61B 2017/1103; A61B 2017/081
    See application file for complete search history.

(56) References Cited

U.S. PATENT DOCUMENTS

| | | | |
|---|---|---|---|
| 2002/0062130 A1* | 5/2002 | Jugenheimer | A61B 17/1285 606/142 |
| 2007/0049967 A1 | 3/2007 | Sibbitt, Jr. et al. | |
| 2020/0397445 A1 | 12/2020 | Shikhman et al. | |

FOREIGN PATENT DOCUMENTS

| | | |
|---|---|---|
| CN | 107693059 | 2/2018 |
| CN | 108577917 | 9/2018 |
| CN | 110123408 | 8/2019 |
| CN | 111281467 A | 6/2020 |
| CN | 212089655 | 12/2020 |
| CN | 112790805 | 5/2021 |
| CN | 213606606 | 7/2021 |
| CN | 215129371 | 12/2021 |
| JP | 2009233314 | 10/2009 |
| WO | 0141623 | 6/2001 |

OTHER PUBLICATIONS

First Office Action from CN Corresponding Application 202110114886.2 issued on Jul. 23, 2024 from the CNIPA. (8 pages) (English Translation Attached).

Extended European Search Report of EP Corresponding Application 22726379.5 issued on Apr. 18, 2024 from the EPO.

\* cited by examiner

FETCHING ASSEMBLY AND RELEASING ASSEMBLY FOR ANASTOMOSIS CLAMP

CROSS-REFERENCE TO RELATED APPLICATIONS

The present application is a continuation of International application No. PCT/CN2022/071619 filed on Jan. 12, 2022 which claims the priority of the Chinese application No. 202110114886.2 entitled "FETCHING ASSEMBLY AND RELEASING ASSEMBLY FOR ANASTOMOSIS CLAMP" and filed on Jan. 28, 2021, both of which are incorporated herein by reference in their entireties.

FIELD

The present disclosure relates to the technical field of medical devices, and more particularly, to a fetching assembly for an anastomosis clamp and a releasing assembly for an anastomosis clamp.

BACKGROUND

An anastomosis clamp is a device used in medical operations to replace the conventional manual suture. With development of modern technology and improvement of manufacturing technology, the current anastomosis clamp in clinical use is highly favored and recommended by clinical surgeons around the world, owing to its reliable quality, convenience in use, especially its clinical advantages such as quick suture, simple operation, less adverse effects and less complications, and foci resection in surgeries involving tumor which could not be realized in the past.

In the prior art, the anastomosis clamp is often disposed in a transparent cap, and a push rod for pushing the anastomosis clamp is also disposed in the transparent cap, making the size of the transparent cap overlarge and thus causing discomfort to the patient when delivering the transparent cap into the body of the patient. To address this problem, some anastomosis clamps are sleeved on the transparent cap. To prevent the anastomosis clamp from getting off, the anastomosis clamp must be assembled on the transparent cap firmly without looseness, which causes difficulties and failures when releasing the anastomosis clamp. It is desirable to design a sleeve-type anastomosis clamp assembly which can achieve easy release of the anastomosis clamp.

The anastomosis clamp plays an important role in modern medical field. In a common anastomosis clamp, the spinous part in a front end of the anastomosis clamp pierces into the tissue and a firm clamping can be achieved. However, the anastomosis clamp is difficult to release. This raises a higher requirement on operational proficiency of an operator since accurately clamping a perforated tissue needs to be achieved by once operation. If a tissue at an incorrect position is clamped, it would be very difficult to release the anastomosis clamp, and serious damages to the tissue may occur when a release is performed. Thus, it is desirable to provide a fetching assembly for the anastomosis clamp by which the anastomosis clamp can be fetched out easily without possible damages to the tissue.

SUMMARY

In the prior art, it is quite difficult to release an anastomosis clamp from a tissue after the anastomosis clamp clamps the tissue, and it would raise a higher requirement on operational proficiency of an operator. The present disclosure provides a fetching assembly for an anastomosis clamp to overcome the above problems.

In order to address these problems, the present disclosure provides technical solutions as follows. A fetching assembly for an anastomosis clamp includes a fetching cap, a fetching hook and an anastomosis clamp. The fetching cap is configured to be mounted on a front end of an endoscope, a front end of the fetching cap is configured to be accommodated in the anastomosis clamp, and the fetching cap is configured to pass through the fetching cap and to hook onto the anastomosis clamp. When the fetching hook is pulled backward, the fetching hook drives the anastomosis clamp to be sleeved on an outer peripheral surface of the front end of the fetching cap.

Further, the anastomosis clamp includes a clamp body and a fetching thread. A front end of the clamp body is closable. A rear end of the clamp body is provided with a plurality of threading holes along a circumferential direction thereof. The fetching thread is configured to pass through the threading hole to be fixed to the clamp body.

Further, a plurality of fetching threads are provided and are connected with each other, and a connection point of the plurality of fetching threads is located on a central axis of the clamp body.

Further, the fetching hook includes a handle and a hook part located at a front end of the handle.

Further, the fetching hook further includes a sliding ring and a pull rope. The sliding ring is slidably connected to the handle. The handle includes an axial hole penetrating through the front end of the handle. The pull rope includes one end connected with the sliding ring and another end connected with the hook part.

Further, the fetching cap includes a fetching cap body and a fixer fixed at a rear end of the fetching cap body. The fixer is configured to be mounted at the front end of the endoscope. A front end of the fetching cap body is provided with two or more slots.

Further, the front end of the fetching cap body is provided with an arc-shaped chamfer.

Preferably, the two or more slots extend along an axial direction of the fetching cap.

Preferably, two sides of each of the two or more slots are provided, at the front end of the fetching cap body, with a chamfered oblique surface.

Preferably, the two or more slots have one-to-one correspondence with the plurality of threading holes.

In the prior art, the transparent cap matching with the anastomosis clamp has a overlarge size, causing discomfort to the patient, or the anastomosis clamp being provided outside causes that the release of the anastomosis clamp often fails. In order to address these problems, the present disclosure provides a releasing assembly for an anastomosis clamp.

The present disclosure further provides a releasing assembly for an anastomosis clamp. The releasing assembly is configured to be used in cooperation with an endoscope and to release the anastomosis clamp by use of the endoscope to clamp a target tissue. The releasing assembly includes a transparent loading cap and a push rod. The anastomosis clamp is configured to be sleeved on a front end of the transparent loading cap. The transparent loading cap is penetrated therethrough along a central axis in a longitudinal direction thereof. The transparent loading cap is provided with a supporting part. The supporting part is provided with a push hole penetrating therethrough in an axial direction. The push rod is configured to pass through the push hole and to move in the axial direction of the push hole to allow one end of the push rod to abut against a rear end of the anastomosis clamp. When an acting force with a preset value is applied to the push rod, the anastomosis clamp is pushed to be detached from the front end of the transparent loading cap to release the anastomosis clamp and to clamp the target tissue.

Further, the supporting part is provided on a side wall of the transparent loading cap. The front end of the transparent loading cap is further provided with a loading ring. The loading ring is made from hard metal material. When the anastomosis clamp is mounted onto the transparent loading cap, a front end of the anastomosis clamp abuts against an outer wall of the loading ring.

Further, the push rod includes a rod body and a push handle connected with one end of the rod body, and another end of the rod body is configured to abut against the rear end of the anastomosis clamp.

Further, the transparent loading cap includes a main body. The main body is penetrated therethrough along a central axis in the axial direction and is made from transparent or semitransparent material. One end of the main body is provided with a sleeve-connected segment configured to be sleeved with the anastomosis clamp. The push hole is located in rear of the sleeve-connected segment. The loading ring is provided closer to a front end of the sleeve-connected segment and is located at the outer side of the main body.

Further, the front end of the sleeve-connected segment is provided with an oblique surface, and an outer side of the sleeve-connected segment that is in rear of the oblique surface is provided with a ring-shaped groove configured to hold the loading ring.

Further, the loading ring is fixedly connected at an end of the sleeve-connected segment.

Further, the loading ring is configured as a taper-shaped structure with an outer diameter gradually decreasing from the rear to the front.

Further, the main body further includes a position-limiting segment connected with the sleeve-connected segment. The position-limiting segment has an outer diameter greater than that of the sleeve-connected segment, and the push hole is located on the position-limiting segment.

Further, the loading ring is adhered or snap-fitted to the ring-shaped groove.

A fetching assembly for an anastomosis clamp is provided. The fetching assembly is configured to be used in cooperation with an endoscope and fetch the anastomosis clamp by use of the endoscope. The anastomosis clamp includes a clamp body and a fetching thread. A front end of the clamp body is configured to be closed in a natural state, a rear end of the clamp body is provided with at least two threading holes along a circumferential direction thereof, and the fetching thread is configured to pass through the at least two threading holes (303) to be fixed to the clamp body. The fetching assembly includes a fetching cap penetrated therethrough in a front-rear direction thereof, and a fetching hook configured to move along an internal axis of the fetching cap in the front-rear direction. The fetching cap is configured to be mounted on a front end of the endoscope, a front end of the fetching cap is configured to be sleeved with the anastomosis clamp. The fetching hook is configured to pass through the fetching cap and hook onto the fetching thread. When the fetching hook is pulled to drive the fetching thread to move backward, the fetching hook drives the anastomosis clamp to be sleeved on an outer peripheral surface of the front end of the fetching cap to allow the front end of the anastomosis clamp to be in an opened state.

Further, the fetching cap includes a fetching cap body and a fixer fixed at a rear end of the fetching cap body. The fixer is configured to be mounted at the front end of the endoscope, and a front end of the fetching cap body is provided with two or more slots.

Further, the fetching assembly further includes a handle. The handle and the fetching hook are connected with each other in relatively fixed way.

Further, a front end of the fetching hook is provided with a hook part. The handle further includes a sliding ring and a pull rope. The sliding ring is slidably connected to the handle, the handle has an axial hole penetrating through the front end of the handle, and the pull rope has one end connected with the sliding ring and another end connected with the hook part.

The present disclosure has advantageous effects as follows.

Firstly, with the fetching assembly for an anastomosis clamp according to the present disclosure, when the anastomosis clamp is pulled out by the fetching hook, the fetching cap can open the anastomosis clamp to allow the spinous part at the front end of the anastomosis clamp to release the tissue, avoiding damages to the tissue when fetching the anastomosis clamp out, greatly lowering the requirement on operational proficiency of an operator, and enabling multiple clamping operations until an optimal clamping position is found.

Secondly, in the fetching assembly for an anastomosis clamp according to the present disclosure, the fetching threads are connected at the rear end of the anastomosis clamp and are connected with each other, and the fetching hook can hook onto the fetching threads at the connection point of the fetching threads to allow the anastomosis clamp to move with the fetching hook.

Thirdly, in the fetching assembly for an anastomosis clamp according to the present disclosure, the front end of the fetching cap is provided with slots, such that when the anastomosis clamp moves outward with the fetching hook, the fetching threads can move along the slots to prevent the fetching threads from bending and to reduce the resistance encountered by the anastomosis clamp.

Fourthly, in the releasing assembly for an anastomosis clamp according to the present disclosure, the anastomosis clamp is provided at the outer side of the transparent cap, the push rod is also provided at the outer side of the transparent cap, so as to reduce the size of the transparent cap and to improve the comfort of the patient. Further, a loading ring made from hard metal material is provided at the front end of the transparent cap, so as to reduce the friction when releasing the anastomosis clamp.

Fifthly, in the releasing assembly for an anastomosis clamp according to the present disclosure, the loading ring made from hard metal is provided at the front end of the anastomosis clamp. When the anastomosis clamp is located on the outer side the transparent cap, the spinous part of the anastomosis clamp is at almost the same height with that of the loading ring. When the anastomosis clamp is released, the spinous part closes and tilts toward the loading ring, and the rigidness of the loading ring can prevent the spinous part from getting into the loading ring to so as to improve the releasing success rate.

Sixthly, in the releasing assembly for an anastomosis clamp according to the present disclosure, the main body is provided with a position-limiting segment connected with the sleeve-connected segment. On one hand, the position-limiting segment can increase the thickness of the wall of the main body to allow the passage of the push rod. On the other hand, the position-limiting segment can limit the anastomosis clamp to go beyond the sleeve-connected segment to avoid the axial movement of the anastomosis clamp and to control the positional relation between the spinous part and the loading ring of the anastomosis clamp.

BRIEF DESCRIPTION OF THE DRAWINGS

The embodiments of the present disclosure will be further illustrated below with reference to the drawings and examples, in which.

REFERENCE NUMERALS

Figure 1:
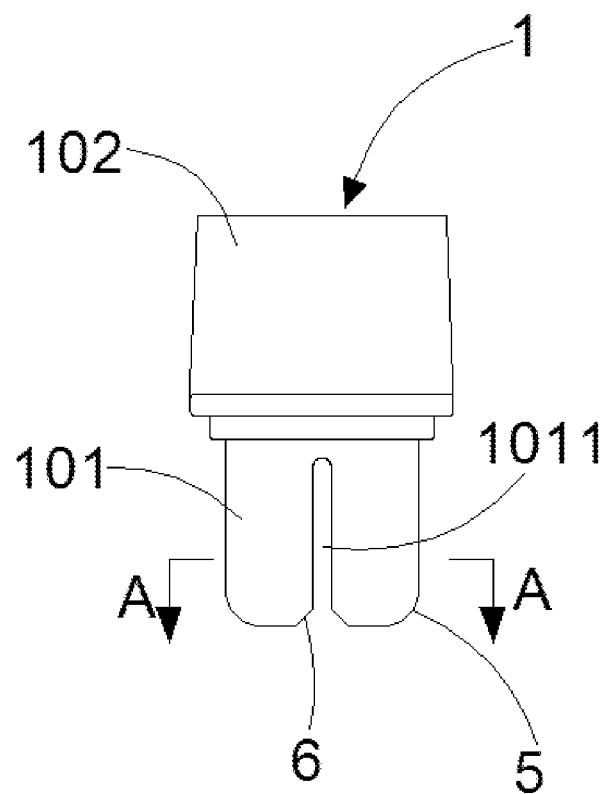
FIG. 1 is a front view of a fetching cap according to an embodiment of the present disclosure.

Fetching cap 1; Fetching cap body 101; Slot 1011; Fixer 102; Fetching hook 2; Handle 201; Hook part 202; Sliding ring 203; Pull rope 204; Anastomosis clamp 3; Clamp body 301; Connection ring 3011; Spinous part 3012; Fetching thread 302; Threading hole 303; Endoscope 4; Arc-shaped chamfer 5; Chamfered oblique surface 6; Perforation 7; Tissue 8; Releasing assembly 9; Transparent loading cap 91; Push rod 92; Push hole 93; Loading ring 94; Supporting part 95; Main body 911; Rod body 921; Push handle 922; Sleeve-connected segment 912; Position-limiting segment 913; Oblique surface 9121.

DETAILED DESCRIPTION

Embodiments of the present disclosure will be described in further detail below. The examples of the embodiments are given in the drawings throughout which same or similar numerals represent same or similar elements or elements with same or similar functions. The embodiments described in the follows with reference to the drawings are exemplary and are only intended to explain the embodiments rather than being construed as limits to the embodiments.

In the description of the embodiments, the term "front end" refers to an end of a surgical instrument closer to a perforation 7 and a tissue 8 during surgery, and the term "rear end" refers to an end of the surgical instrument away from the perforation 7 and the tissue 8 during surgery.

As illustrated in FIG. 1 to FIG. 10, an embodiment provides a fetching assembly for an anastomosis clamp 3. The fetching assembly for the anastomosis clamp includes a fetching cap 1, a fetching hook 2 and an anastomosis clamp 3. The fetching cap 1 is configured to be mounted onto a front end of an endoscope 4. A front end of the fetching cap is configured to be accommodated in the anastomosis clamp, that is, the fetching cap 1 has an outer diameter smaller or equal to an inner diameter of the anastomosis clamp 3. The fetching hook 2 is configured to pass through the fetching cap 1 and to hook onto the anastomosis clamp 3. When the fetching hook 2 is pulled backward, the fetching hook 2 drives the anastomosis clamp 3 to be sleeved on an outer peripheral surface of the front end of the fetching cap 1. The fetching cap 1 has a tube-shaped structure and the anastomosis clamp 3 is able to be sleeved on the outer peripheral surface of the fetching cap 1.

When the anastomosis clamp 3 which is clamping the tissue 8 is needed to be fetched out, the fetching cap 1 is brought to the anastomosis clamp 3 by the endoscope 4, the fetching hook 2 passes through the fetching cap 1 along the channel of the endoscope 4, and hooks onto the anastomosis clamp 3. The anastomosis clamp 3 can be pulled backward by the fetching hook 2. The anastomosis clamp 3 is coaxial with the fetching cap 1, the spinous part 3012 of the anastomosis clamp 3 can be opened gradually by the fetching cap 1 when the anastomosis clamp 3 moves backward to allow the anastomosis clamp 3 to be separated from the tissue 8 until the anastomosis clamp 3 is completely sleeved on the fetching cap 1. Then, the fetching hook 2 can be detached from the anastomosis clamp 3 and can be pulled out, and the anastomosis clamp 3 can be fetched out along with the endoscope 4. In the embodiment, when the anastomosis clamp 3 is pulled out, the spinous part 3012 of the anastomosis clamp 3 can be opened so as to avoid tear at and damage to the tissue 8 and thus enable clamping the tissue 8 repeatedly.

Figure 3:
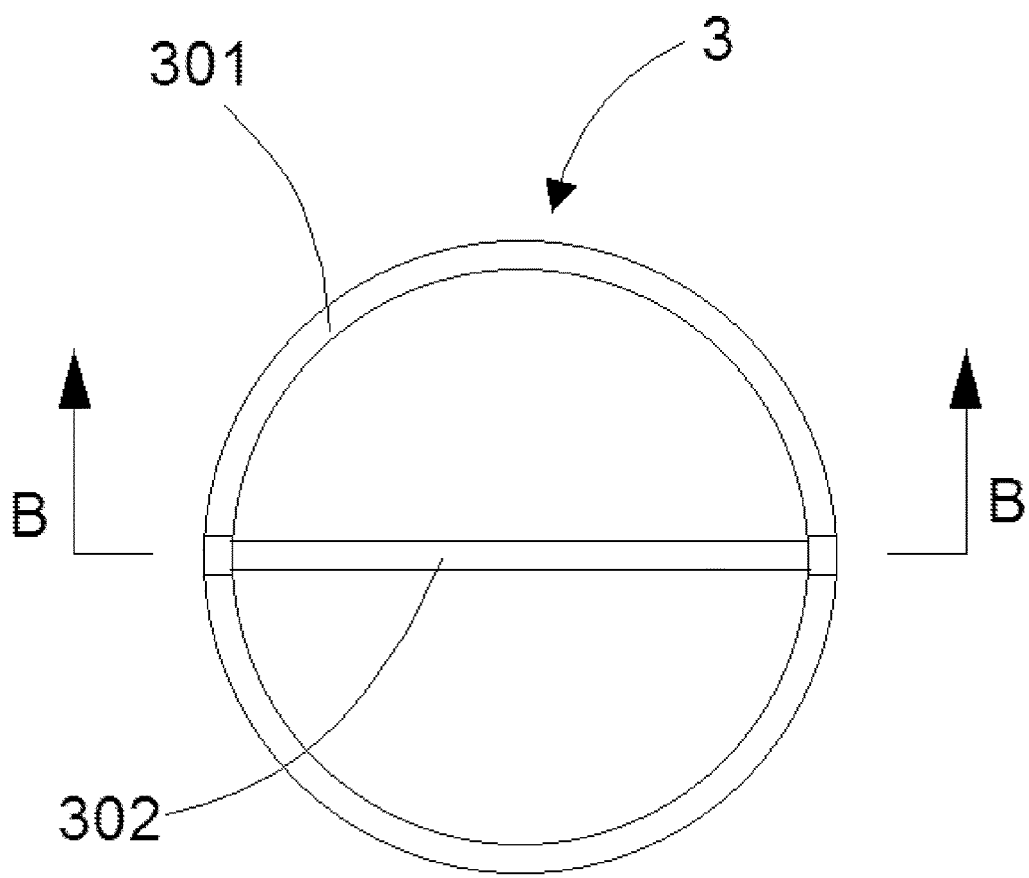
FIG. 3 is a top view of an anastomosis clamp having two threading holes.
Figure 4:
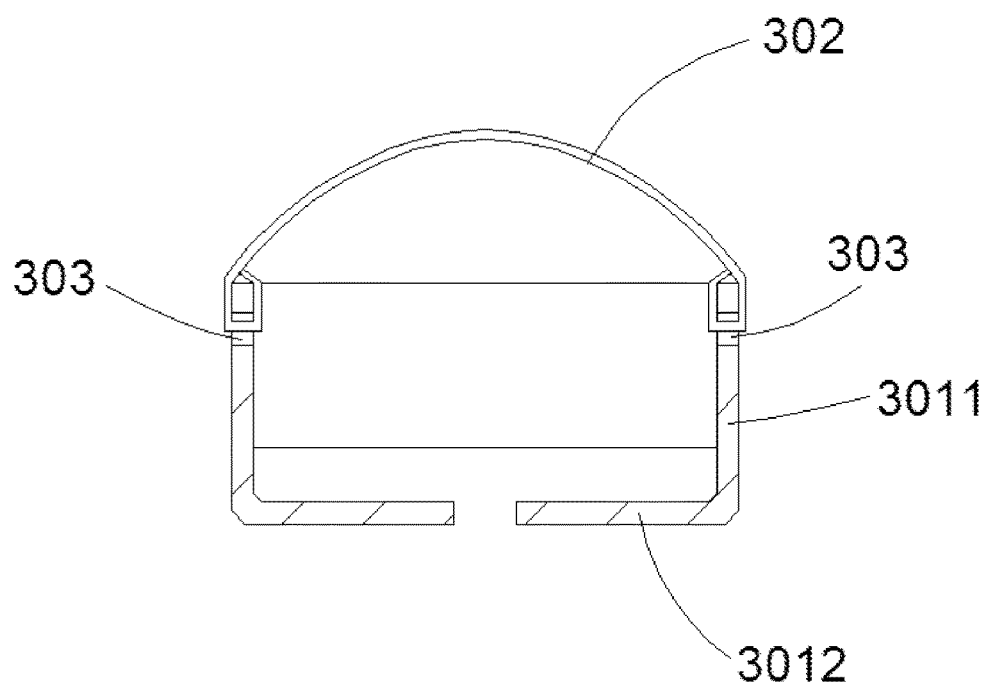
FIG. 4 is a sectional view taken along the direction of B-B in FIG. 3.
Figure 5:
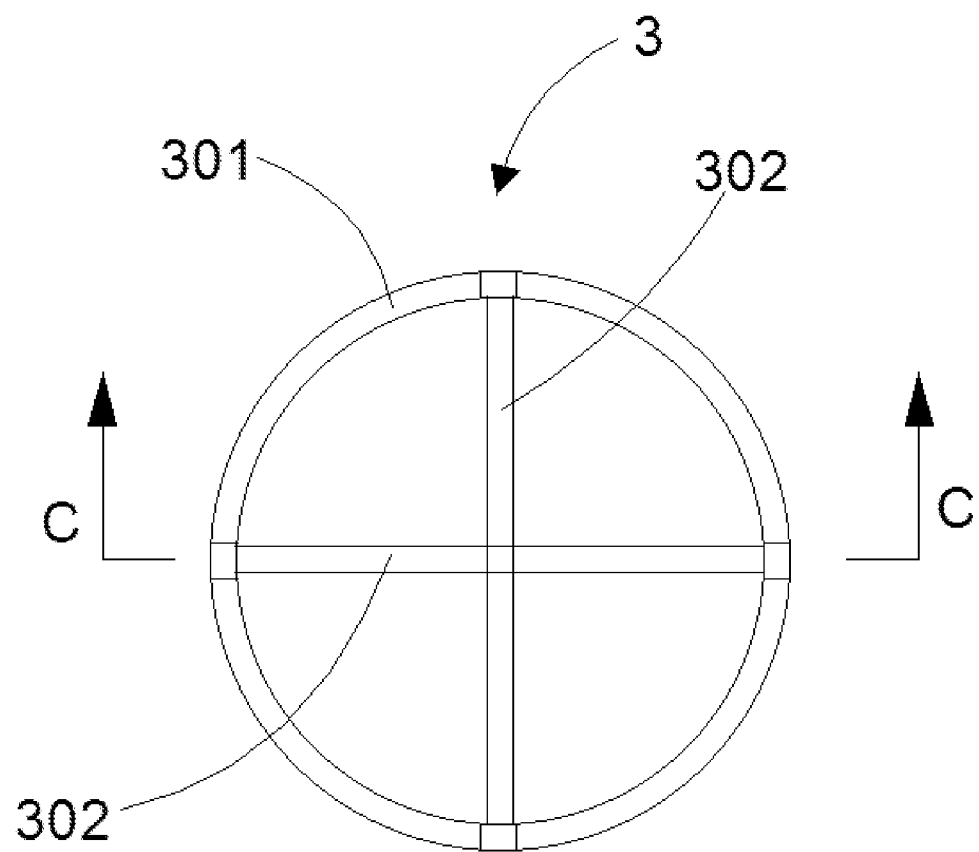
FIG. 5 is a top view of an anastomosis clamp having four threading holes.
Figure 6:
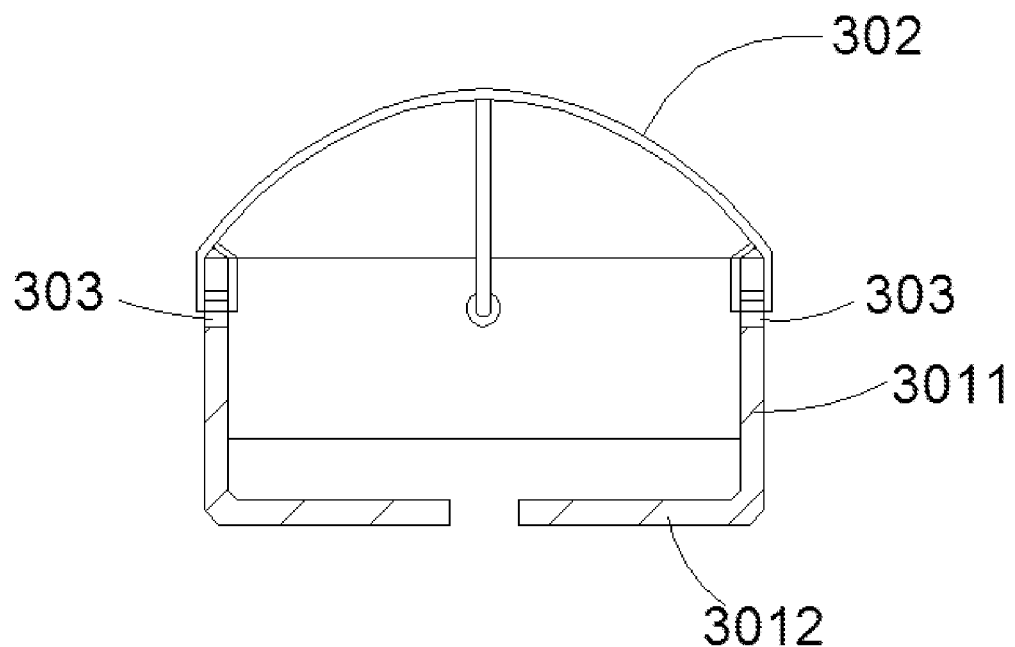
FIG. 6 is a sectional view taken along the direction of C-C in FIG. 3.
Figure 7:
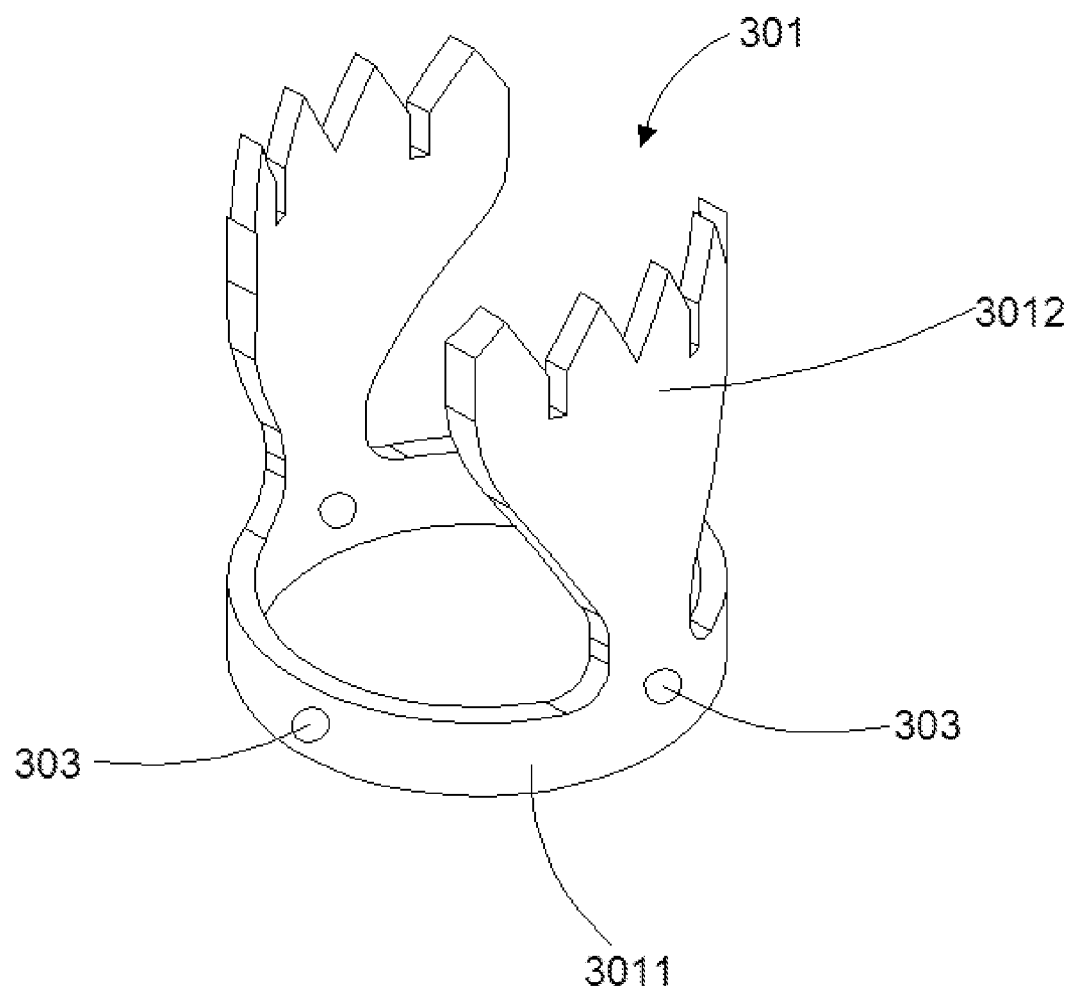
FIG. 7 is a schematic view illustrating a structure of a clamp body of the anastomosis clamp as illustrated in FIG. 5.
Figure 8:
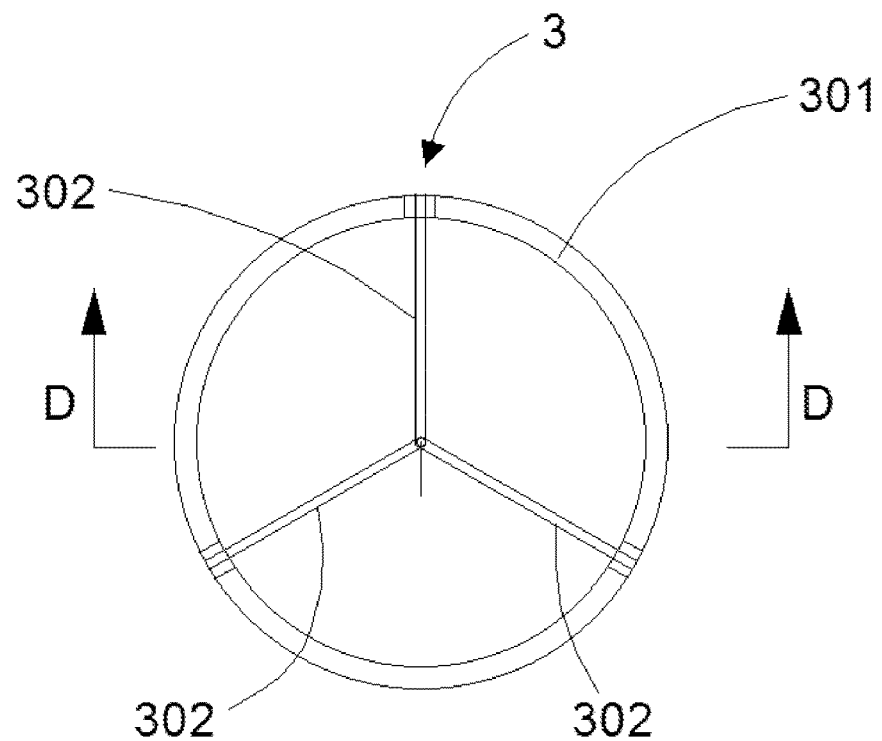
FIG. 8 is a top view of an anastomosis clamp having three threading holes.
Figure 9:
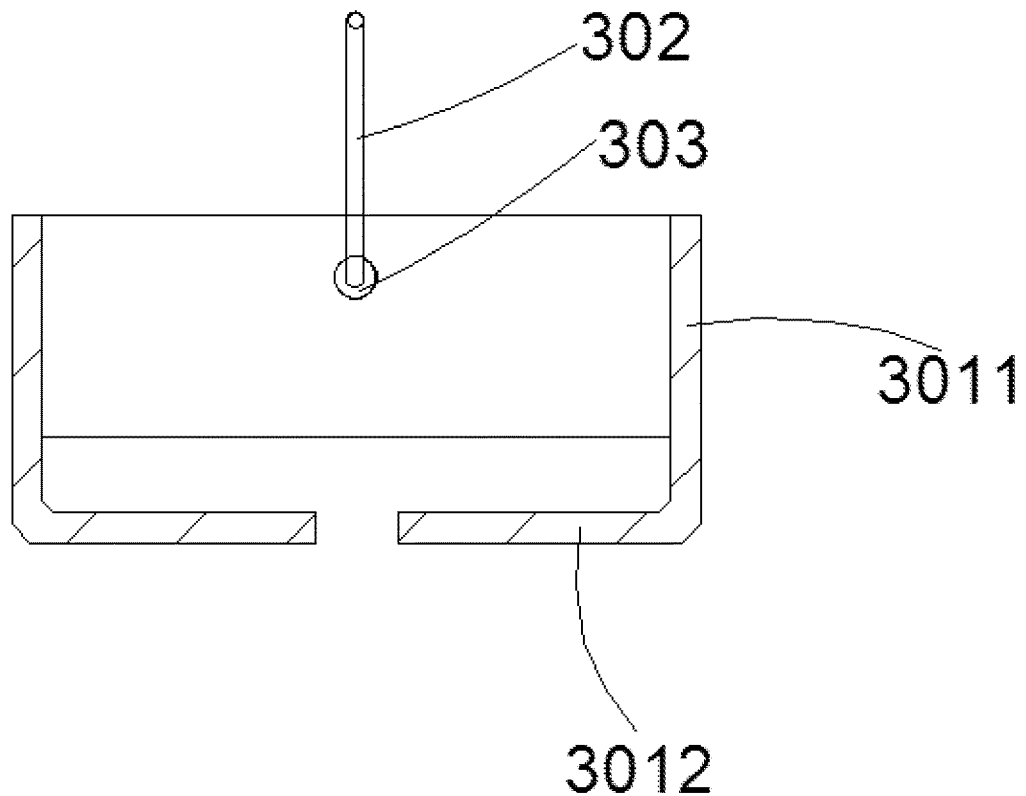
FIG. 9 is a sectional view taken along the direction of D-D in FIG. 8.

The anastomosis clamp 3 may be of but not limited to a structure as follows. The anastomosis clamp 3 includes a clamp body 301 and a fetching thread 302. A front end of the clamp body 301 is closable, a rear end of the clamp body 301 is provided with a plurality of threading holes 303 along a circumferential direction thereof. The fetching thread 302 is configured to pass through at least one of the plurality of threading holes 303 to be fixed to the clamp body 301. The anastomosis clamp 3 is perforated axially. The clamp body 301 usually includes a connection ring 3011 and a spinous part 3012. The plurality of threading holes 303 are located on the connection ring 3011. The spinous part 3012 is located at a front end of the connection ring 3011, is composed of at least two spinous claws, and may be made from shape memory material. When no external force is applied, the front end of the spinous part 3012 is in a closed and clamping state. The spinous claw may be of a taper-shaped or tooth-shaped structure. In the anastomosis clamp 3 as illustrated in FIG. 7, the spinous claws are tooth-shaped structures. Two or more threading holes 303 may be provided, a plurality of fetching threads 302 may be provided and be connected with each other, and the connection point of the plurality of fetching threads 302 is located on a central axis of the clamp body 301. As illustrated in FIG. 3 and FIG. 4, the anastomosis clamp 3 is provided with two threading holes 303, and two ends of one fetching thread 302 are connected to the two threading holes 303. As illustrated in FIG. 5 and FIG. 6, the anastomosis clamp 3 is provided with four threading holes 303, and either of two fetching threads 302 is connected to two opposite threading holes 303, and the two fetching threads 302 are intersected and connected on the central axis of the clamp body 301. As illustrated in FIG. 8 and FIG. 9, the anastomosis clamp 3 is provided with three threading holes 303, three fetching threads 302 are connected to the three threading holes 303 respectively at one end thereof, and the three fetching threads 302 are intersected and connected on the central axis of the clamp body 301 at the other end thereof. By providing the connection point of the fetching threads 302 on the central axis of the clamp body 301, the fetching hook 2 can directly hook onto the connection point of the fetching threads 302 after extending into the endoscope 4, eliminating the need for bending of the fetching hook 2 and searching for the fetching threads.

Figure 10:
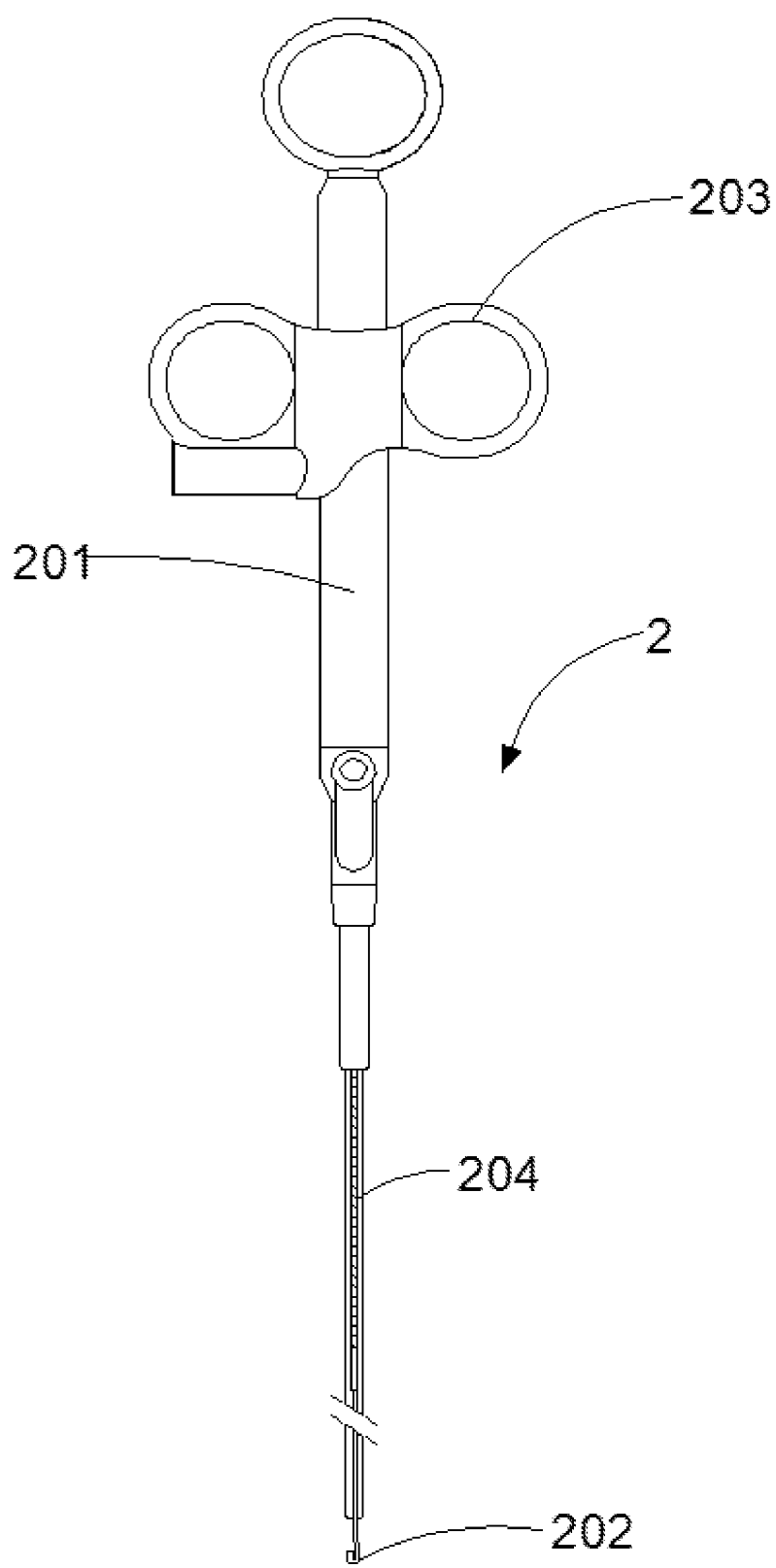
FIG. 10 is a schematic view illustrating a structure of a fetching hook according to an embodiment of the present disclosure.

As illustrated in FIG. 10, the fetching hook 2 includes a handle 201 and a hook part 202 at a front end of the handle 201. The hook part 202 may be directly fixed at the front end of the handle 201. In one embodiment of the present disclosure, the hook part 202 is movably connected with the handle 201, and when the handle 201 is fixed, the position of the hook part 202 in the front-rear direction can be finely adjusted. In particular, the fetching hook 2 further includes a sliding ring 203 and a pull rope 204. The sliding ring 203 is slidably connected to the handle 201. The handle 201 has an axial hole penetrating through the front end of the handle 201. The pull rope 204 has one end connected with the sliding ring 203 and another end connected with the hook part 202. When the fetching hook 2 reaches a target position through the channel of the endoscope 4, the position of the hook part 202 can be finely adjusted by pushing the sliding ring 203 in the front-rear direction.

Figure 2:
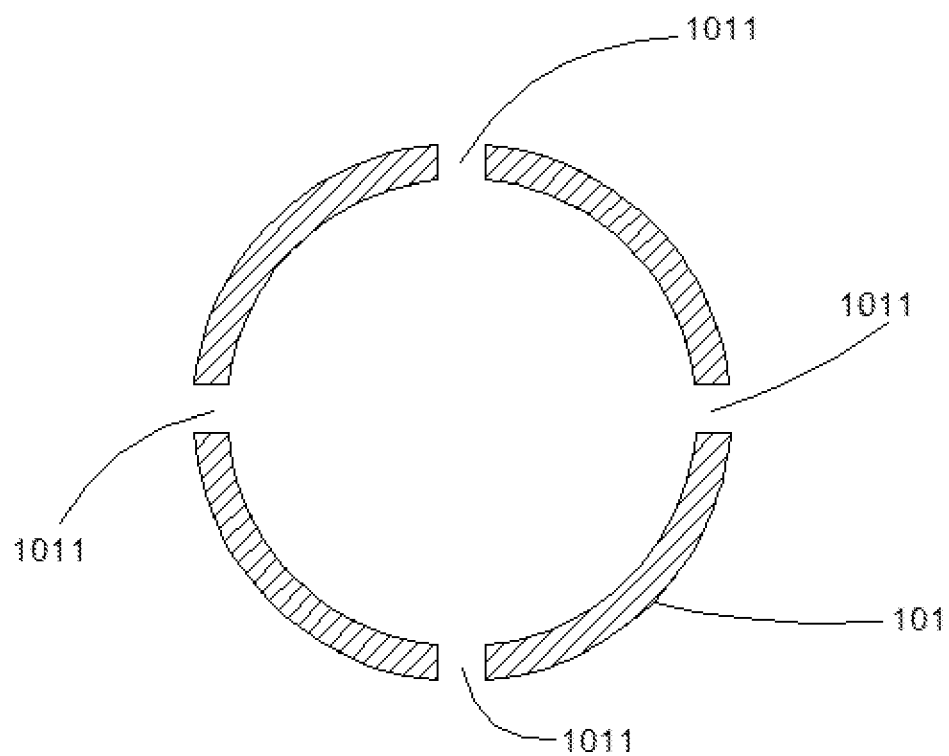
FIG. 2 is a sectional view taken along the direction of A-A in FIG. 1.

As illustrated in FIG. 1 and FIG. 2, the fetching cap 1 includes a fetching cap body 101 and a fixer 102 fixed at a rear end of the fetching cap body 101. The fixer 102 is configured to be mounted at the front end of the endoscope 4, the front end of the fetching cap body 101 is provided with two or more slots 1011. The fixer 102 is a ring-shaped structure. Since the fixer 102 is mounted fixedly to the endoscope 4, the specific structure of the fixer 102 may be designed according to different models of the endoscopes 4. When the anastomosis clamp 3 is fetched out, the anastomosis clamp 3 is sleeved on the out peripheral surface of the fetching cap body 101. Each of the two or more slots 1011 is configured to give way to the fetching thread 302. Since the anastomosis clamp 3 is driven by the fetching thread 302 to move backward, if the fetching cap body 101 is a complete tube-shaped structure, it would be difficult for the anastomosis clamp 3 to move backward and to be sleeved on the outer peripheral surface of the fetching cap body 101 because the anastomosis clamp 3 is obstructed by the front end of the fetching cap body 101. Therefore, provision of the two or more slots 1011 is needed, so as to allow the fetching thread 302 to move backward gradually. Preferably, the two or more slots 1011 extend along the axial direction of the fetching cap 1. The two or more slots 1001 can be distributed randomly. The fetching thread 302 may correspond to a slot 1011 by rotating the fetching hook 2, so as to allow the fetching thread 302 to be caught into the slot 1011. In a preferred embodiment, the two or more slots 1011 have one-to-one correspondence with the plurality of threading holes 303, that is, the number of the two or more slots 1011 is the same with that of the plurality of threading holes 303 and a line connecting each of the two or more slots 1011 and its corresponding threading hole 303 is parallel with the central axis of the fetching cap 1.

Preferably, the front end of the fetching cap body 101 is provided with an arc-shaped chamfer 5. As illustrated in FIG. 1, the arc-shaped chamfer 5 is located at an outer peripheral edge of the fetching cap body 101. When the anastomosis clamp 3 moves backward to be sleeved on the outer peripheral surface of the fetching cap 1, the anastomosis clamp 3 firstly contacts with the arc-shaped chamfer 5. The arc-shaped chamfer 5 provides a guiding and transition function and avoids damages to a human body cavity or scratches to the surface of the anastomosis clamp 3.

Preferably, two sides of each of the two or more slots 1011 are provided, at the front end of the fetching cap body 101, with a chamfered oblique surface 6. The provision of the chamfered oblique surface 6 allows the front end of the two or more slots 1011 to be an open structure with a larger size, so as to facilitate the fetching threads 302 getting into the slots 1011.

Figure 11:
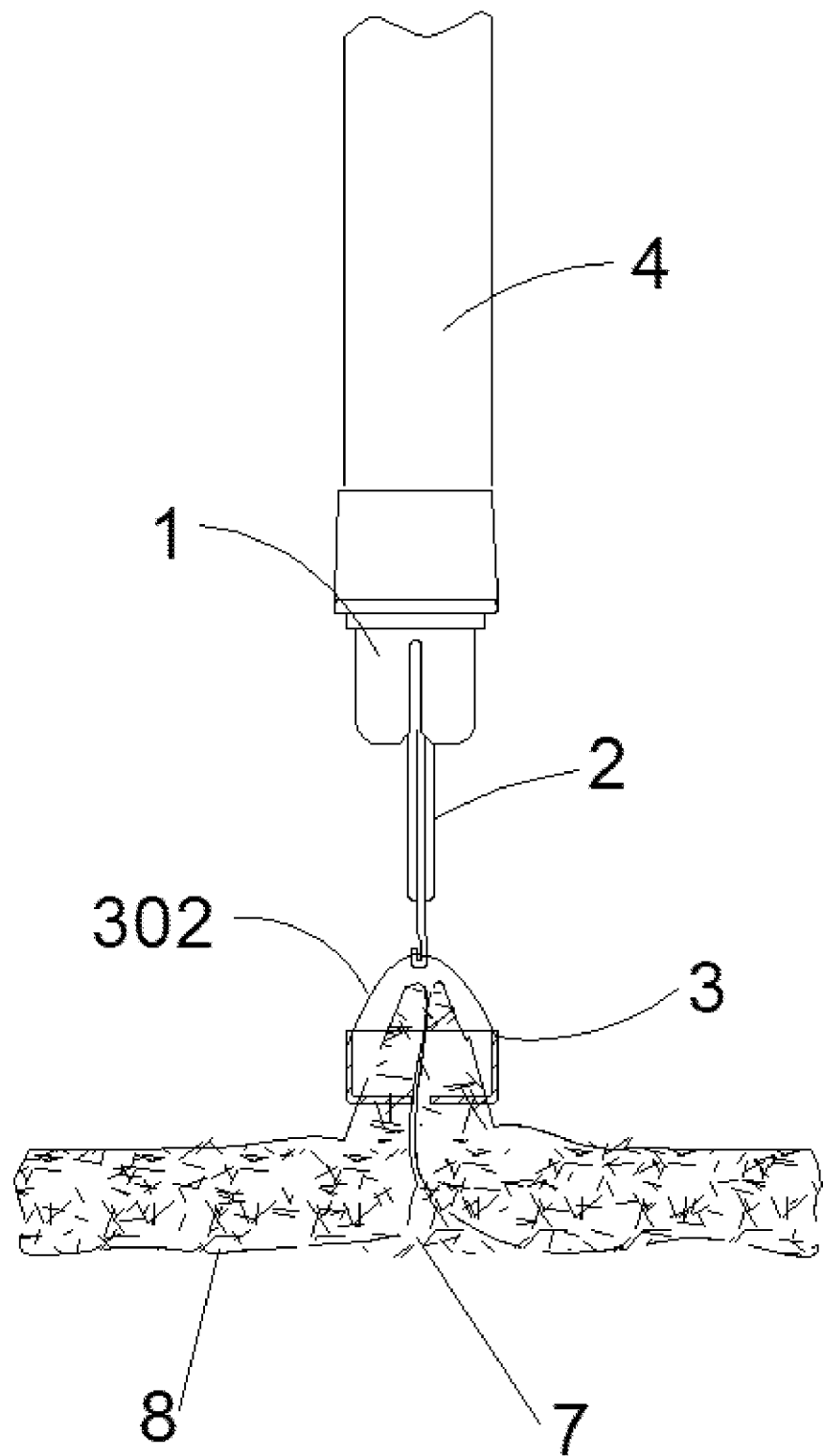
FIG. 11 is a schematic view illustrating a state in which a fetching assembly is ready to be pulled out according to an embodiment of the present disclosure.
Figure 12:
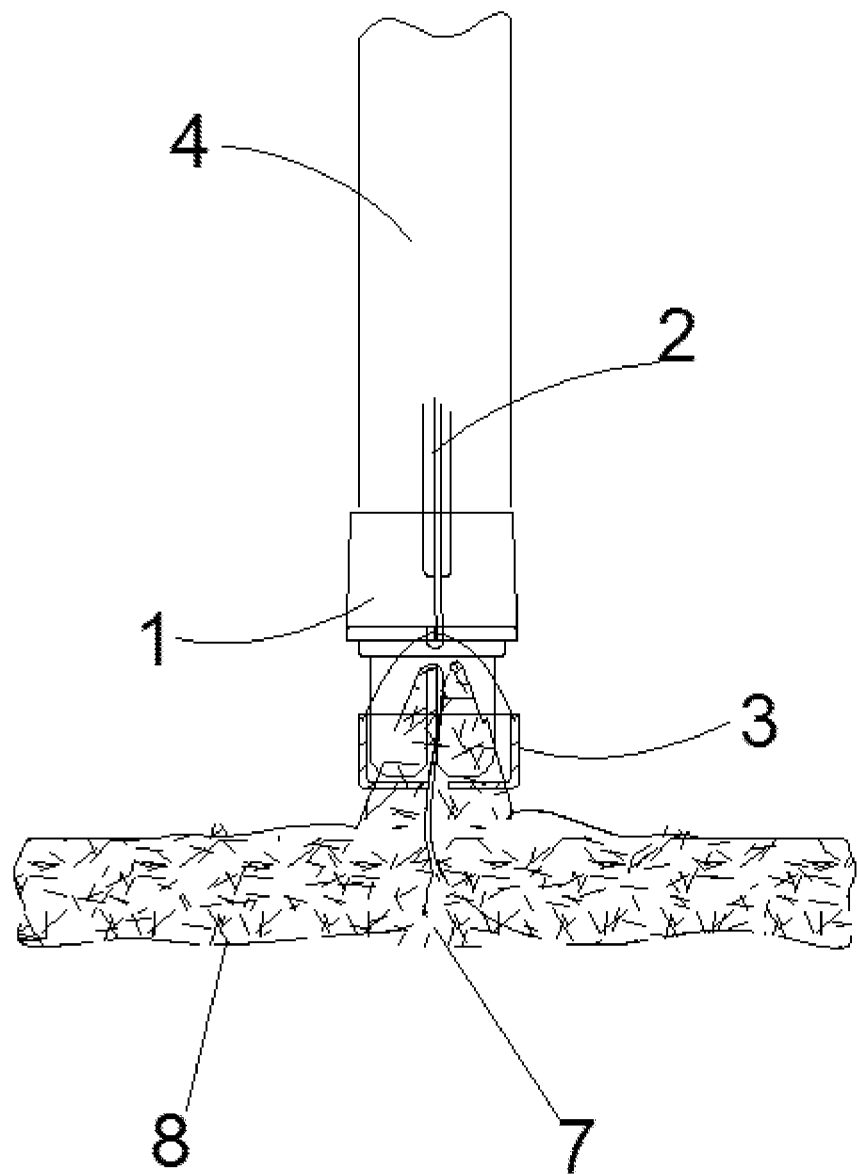
FIG. 12 is a schematic view illustrating a state in which the fetching assembly is ready to be restored according to an embodiment of the present disclosure.
Figure 13:
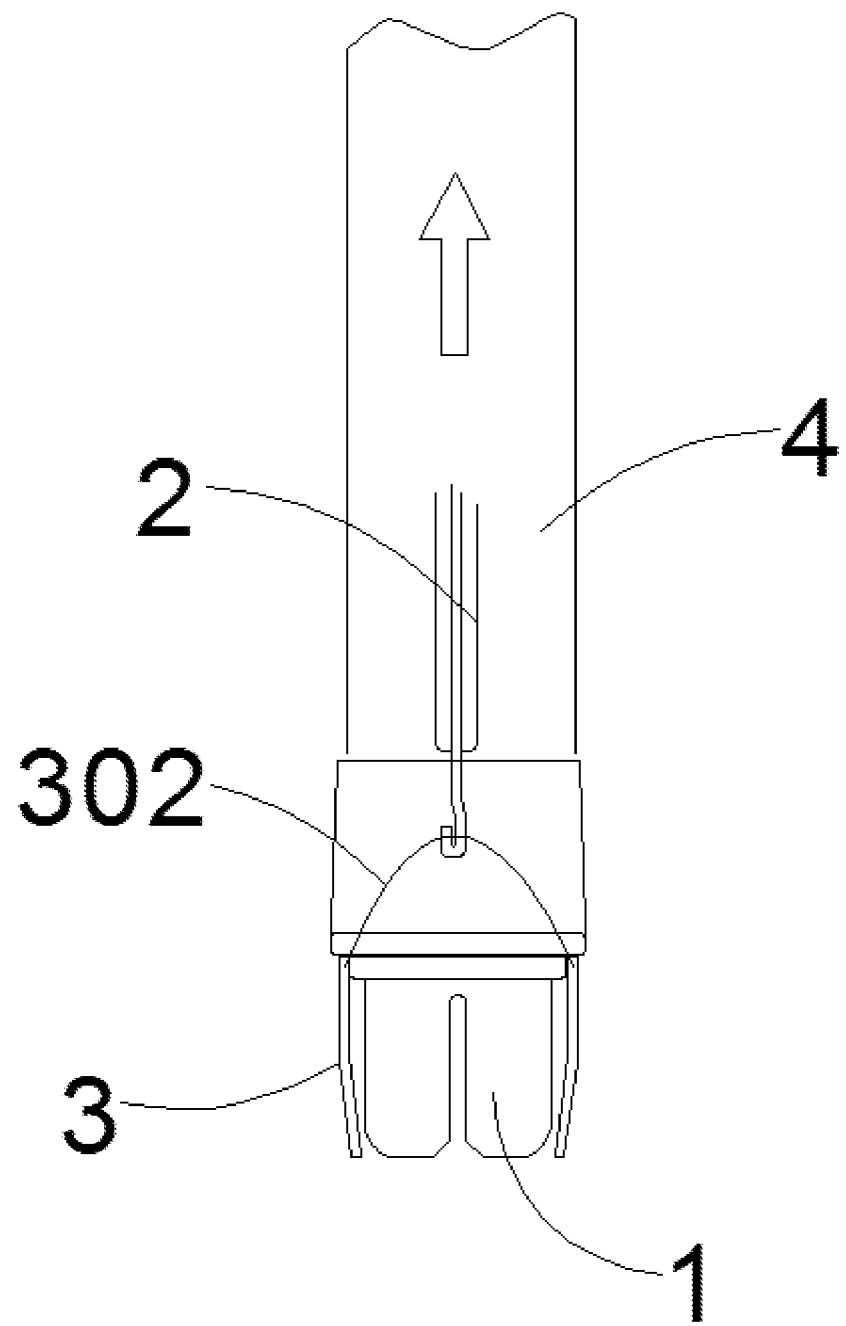
FIG. 13 is a schematic view illustrating a state in which the anastomosis clamp is completely pulled out.

In the present embodiment, the fetching assembly operates based on a principle as follows. A special fetching cap 1 is mounted on the front end of the endoscope 4, and the endoscope 4 is inserted into a target position. The fetching hook 2 is inserted through the channel of the endoscope 4 to allow the fetching hook 2 to extend out of the fetching cap 1, and hooks onto the fetching threads 302 on the anastomosis clamp 3. At this time, the fetching assembly is in a state in which the fetching assembly is ready to be pulled out (as illustrated in FIG. 11). Then the fetching cap 1 is pushed forward or the fetching hook 2 is pulled backward, the fetching hook 2 returns back into the channel of the endoscope 4 until the connection ring 3011 is sleeved on the outer peripheral surface of the fetching cap 1. At this time, the fetching assembly is in a state in which the fetching assembly is ready to be restored, that is, the anastomosis clamp 3 is to be restored (as illustrated in FIG. 12). The fetching hook 2 continues to be pulled, the anastomosis clamp 3 is pulled to be restored through the arc-shaped chamfers 5 at the front end of the fetching cap 1, so as to be remounted onto the fetching cap 1. Then the endoscope 4 can be pulled out of the human body along with the anastomosis clamp 3, thus the anastomosis clamp 3 can be taken out (as illustrated in FIG. 13).

According to another embodiment of the present disclosure, a fetching assembly for an anastomosis clamp is provided. The fetching assembly is configured to be used in cooperation with an endoscope 4 and to fetch the anastomosis clamp 3 in a human body by use of the endoscope 4. The anastomosis clamp 3 includes a clamp body 301 and a fetching thread 302. A front end of the clamp body 301 is configured to be closed in a natural state, and a rear end of the clamp body 301 is provided with at least two threading holes along a circumferential direction thereof. The fetching thread 302 is configured to pass through the at least two threading holes to be fixed to the clamp body 301. The fetching assembly includes a fetching cap 1 penetrated therethrough in a front-rear direction thereof and a fetching hook 2 configured to move along an internal axis of the fetching cap 1 in the front-rear direction. The fetching cap 1 is configured to be mounted on the front end of the endoscope 4. The front end of the fetching cap 1 is configured to be sleeved with the anastomosis clamp 3. The fetching hook 2 is configured to pass through the fetching cap 1 and hook onto the fetching thread 302.

When the fetching hook 2 is pulled to drive the fetching thread 302 to move backward, the fetching hook 2 drives the anastomosis clamp 3 to be sleeved on the outer peripheral surface of the front end of the fetching cap 1, to allow the front end of the anastomosis clamp 3 to be in an opened state.

Compared with the above embodiment, the fetching assembly according to the present embodiment does not include the anastomosis clamp 3, and the anastomosis clamp 3 is considered as an object to be fetched. Because hemostasis is needed when there is a large-area wound in a human tissue, the releasing assembly for an anastomosis clamp is used to clamp the target tissue with the wound by use of the endoscope 4 to stop bleeding. When the hemostasis is finished, in order to avoid any influence on other examinations of the patient caused by the anastomosis clamp 3 made of metal, the anastomosis clamp 3 needs to be fetched out. Thus, the fetching assembly is inserted into the human body by use of the endoscope 4 to fetch out the anastomosis clamp 3.

In one embodiment, as illustrated in FIG. 1, the fetching cap 1 includes a fetching cap body 101 and a fixer 102 fixed at the rear end of the fetching cap body 101. The fixer 102 is configured to be mounted at the front end of the endoscope 4, and the front end of the fetching cap body 101 is provided with two or more slots.

As illustrated in FIG. 10 and FIG. 11, the fetching assembly includes a handle 201. The handle 201 and a fetching hook 2 are connected with each other in relatively fixed way. The front end of the fetching hook 2 is provided with a hook part 202. The handle 201 further includes a sliding ring 203 and a pull rope 204. The sliding ring 203 is slidably connected to the handle 201. The handle 201 has an axial hole penetrating through the front end of the handle 201. A pull rope 20 has one end connected with the sliding ring 203 and another end connected with the hook part 202.

Figure 14:
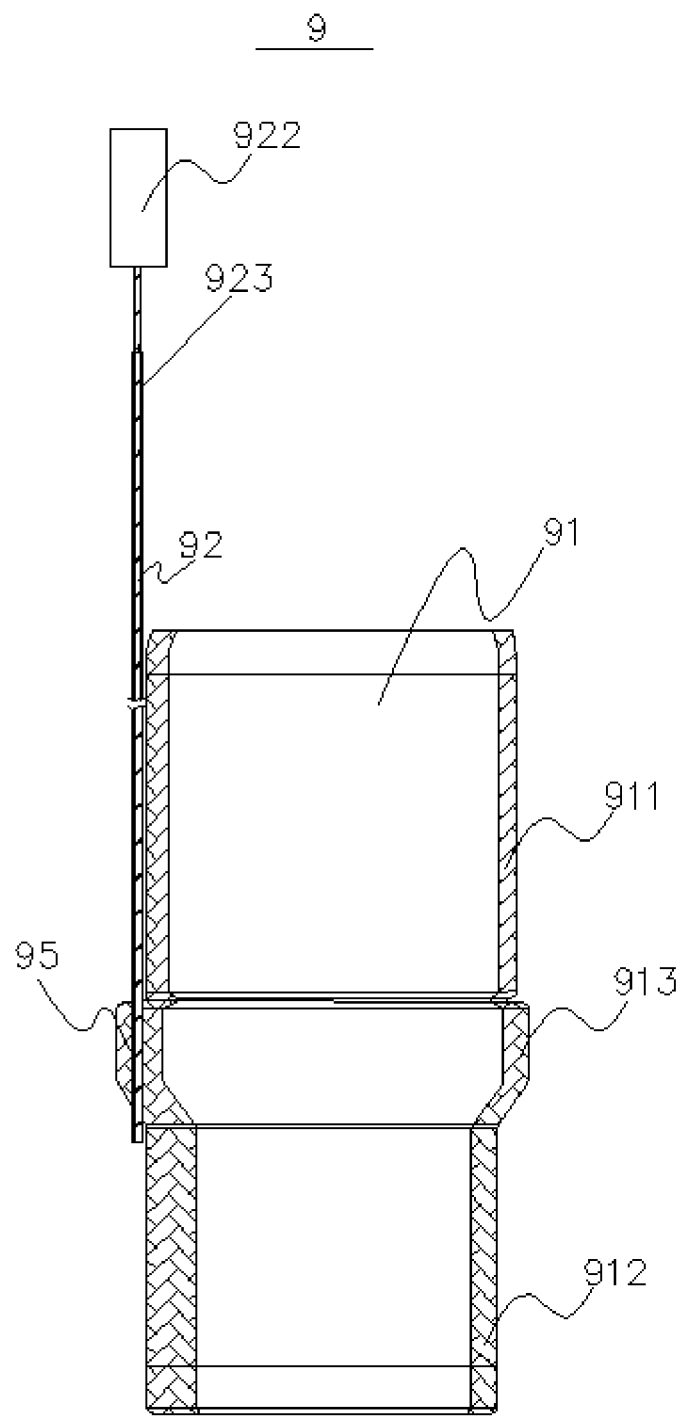
FIG. 14 is a sectional view illustrating an assembled structure of a releasing assembly according to an embodiment of the present disclosure.
Figure 15:
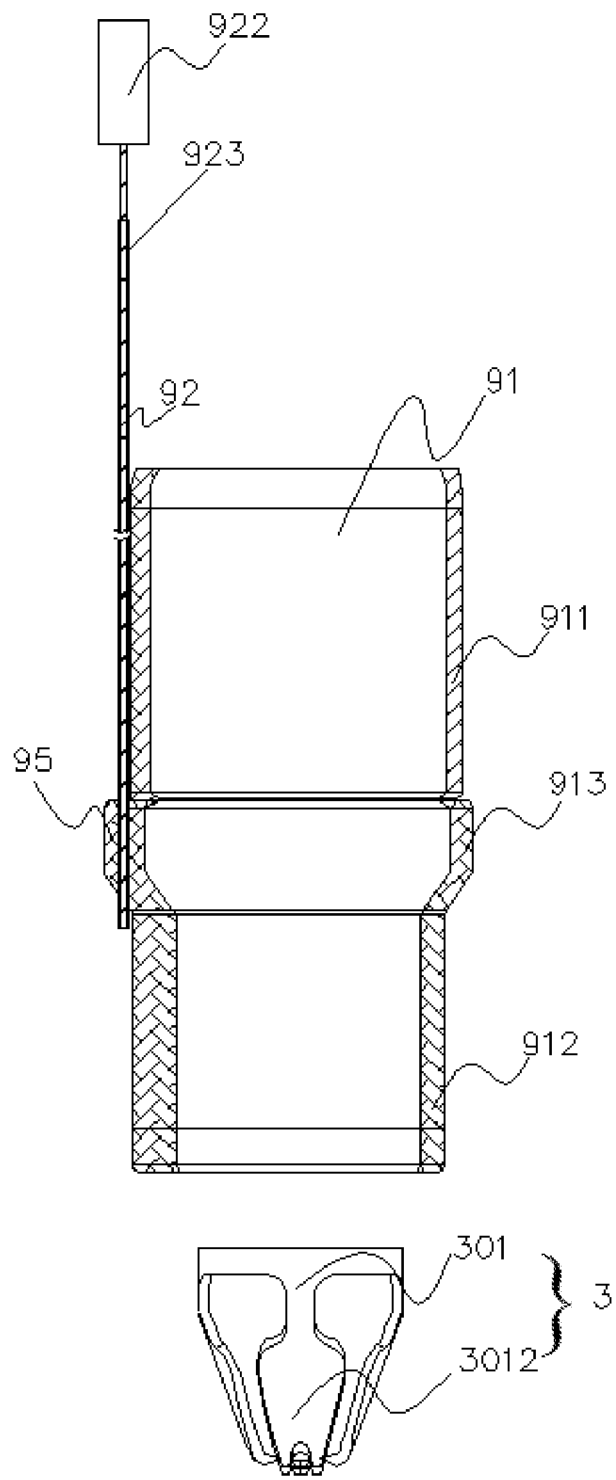
FIG. 15 is a schematic view illustrating a state in which the anastomosis clamp is released by the releasing assembly according to an embodiment of the present disclosure, wherein the releasing assembly is shown in a sectional view.

As illustrated in FIG. 14 and FIG. 15, according to another embodiment of the present disclosure, a releasing assembly 9 for an anastomosis clamp is provided. Similarly with the above mentioned fetching assembly, the releasing assembly 9, as a consumable item to the endoscope 4, needs to be used in cooperation with the endoscope 4. The anastomosis clamp 3 is released by use of the endoscope 4 to clamp the target tissue to achieve the purpose of anastomosis or hemostasis.

Figure 20:
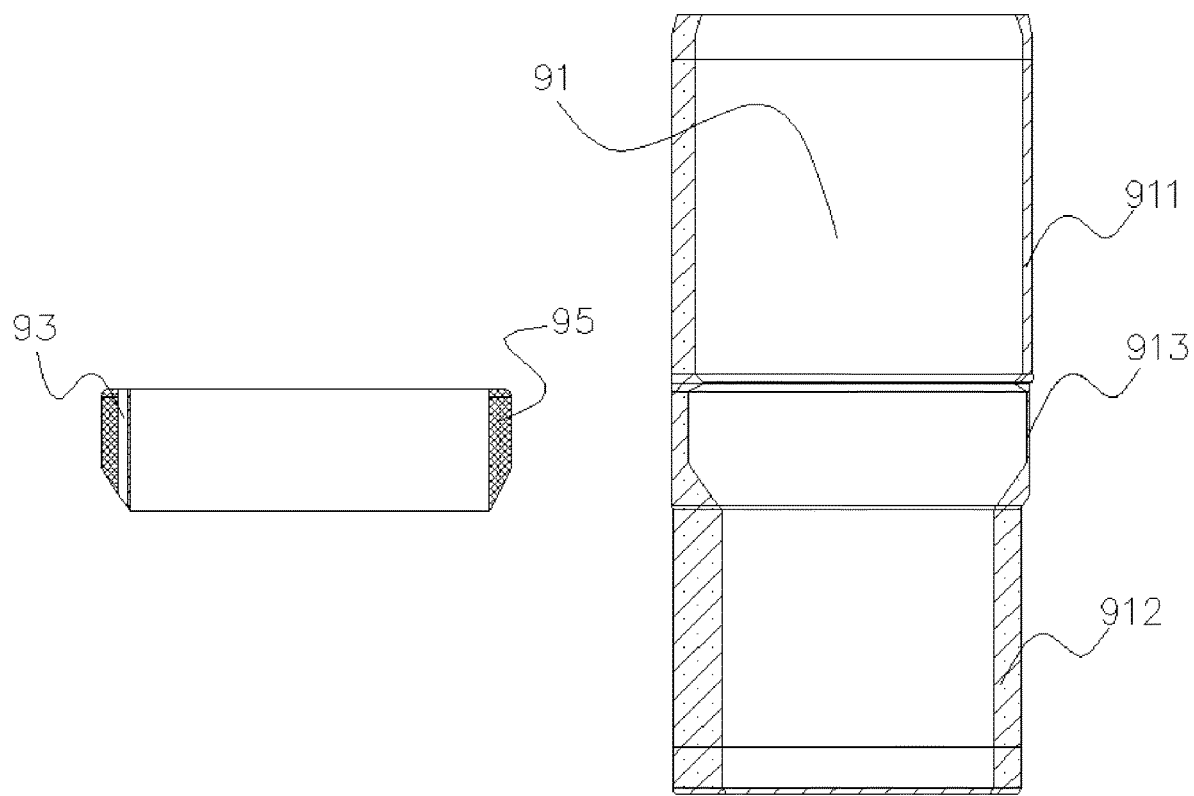
FIG. 20 is a sectional and exploded view illustrating a structure of a transparent loading cap according to an embodiment of the present disclosure.

Referring to FIG. 15 and FIG. 20, the releasing assembly 9 includes a loading transparent cap 91 and a push rod 92. The transparent loading cap 91 is penetrated therethrough along a central axis in a longitudinal direction thereof and is in an almost tube-shaped structure. The anastomosis clamp 3 is configured to be sleeved on a front end of the transparent loading cap 91, and the transparent loading cap 91 can be sleeved on a head end of an endoscope such as a gastroscope or an enteroscope. A supporting part 95 is provided on the transparent loading cap 91 located in rear of the anastomosis clamp 3. The supporting part 95 is provided with a push hole 93 penetrating therethrough along the axial direction. The push rod 92 is configured to move in the axial direction of the push hole 93 to allow one end of the push rod 92 to abut against the rear end of the anastomosis clamp 3. As illustrated in FIG. 20, the supporting part 95 and the transparent loading cap 91 are two separate parts which can be fixed together through adhesion or interference fit.

In another embodiment, a region of the transparent loading cap 91 where the push hole 93 is located may be subject to a wall thickness increasing process, that is, the supporting part 95 can be integrally formed at the side wall of the transparent loading cap 91. In another embodiment not shown in the drawings, the supporting part 95 can be a separate part and can be fixed at the side part of the transparent loading cap 91 through adhesion or snap fit, such that the supporting part 95 becomes a replaceable part, which reduces potential cost for replacement. In the present embodiment, the push rod 92 is configured to pass through the push hole 93 and to move back and forth along the axial direction of the push hole 93 to allow the push rod 92 to abut against the rear end of the anastomosis clamp 3. The push rod 92 can push the anastomosis clamp 3 forward to provide a driving force to release the anastomosis clamp 3.

Figure 16:
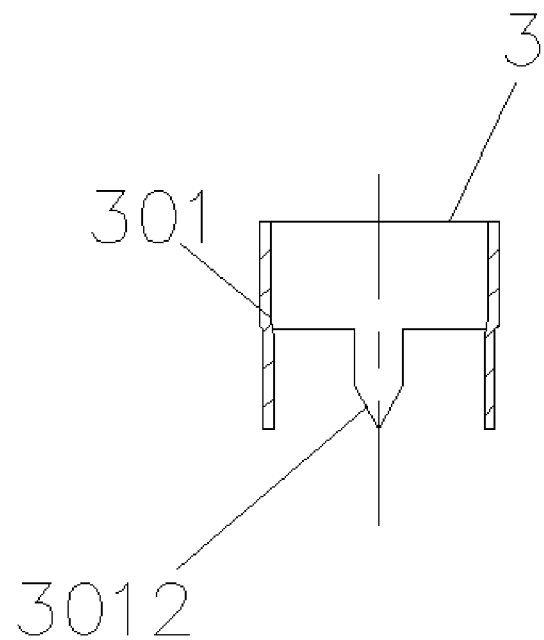
FIG. 16 is a sectional view illustrating a structure of the anastomosis clamp opened by a transparent loading cap according to an embodiment of the present disclosure.
Figure 17:
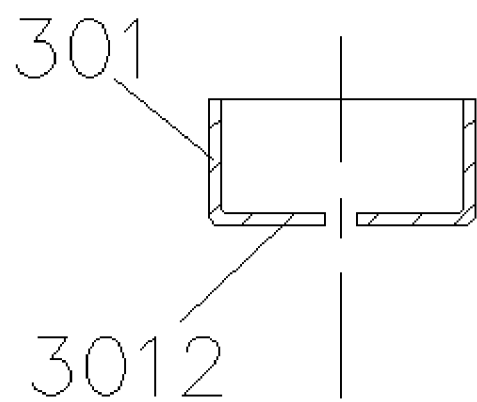
FIG. 17 is a sectional view illustrating a structure of the anastomosis clamp released by the releasing assembly according to an embodiment of the present disclosure.

Referring to FIG. 15 to FIG. 17, the anastomosis clamp 3 is usually made from shape memory alloy, and is configured to clamp a target tissue using the spinous part 3012 with a shape memory property that is in the front end of the anastomosis clamp 3. When the anastomosis clamp 3 is loaded onto the transparent loading cap 91, the spinous part 3012 is opened. When the anastomosis clamp 3 is released, the spinous part 3012 is closed under a shape memory restoration force. The transparent loading cap 91 is an almost tube-shaped structure with a penetrating-through cavity along its central axis. One end of the push rod 92 abuts against the rear end of the anastomosis clamp 3 after passing through the push hole 93 from the rear end of the push hole 93. When the anastomosis clamp 3 is needed to be released, the push rod 92 is pushed forward to provide a driving force that makes the anastomosis clamp 3 move forward. When the spinous part 3012 of the anastomosis clamp 3 starts to be separated from the transparent loading cap 91, the anastomosis clamp 3 can get off from the transparent loading cap 91 in an instant moment under the function of its shape memory alloy, so as to achieve clamping a target tissue or suture of a tissue with a large wound.

Figure 18:
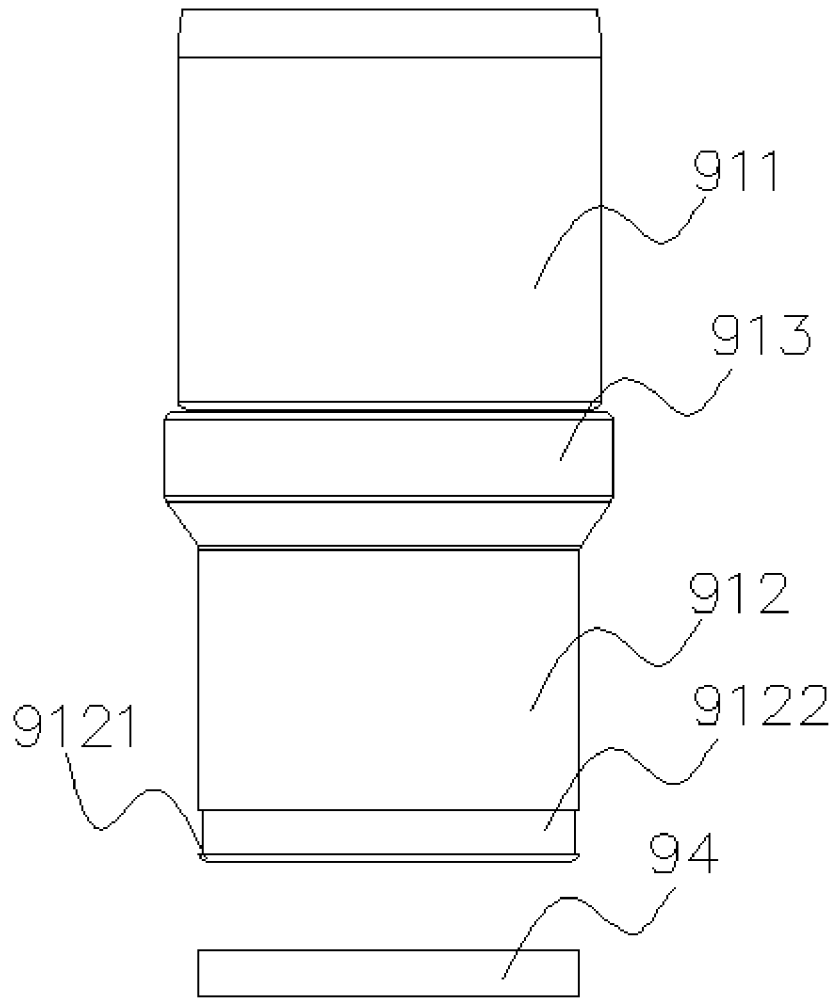
FIG. 18 is a exploded view illustrating a structure of a transparent loading cap and a loading ring according to an embodiment of the present disclosure.
Figure 22:
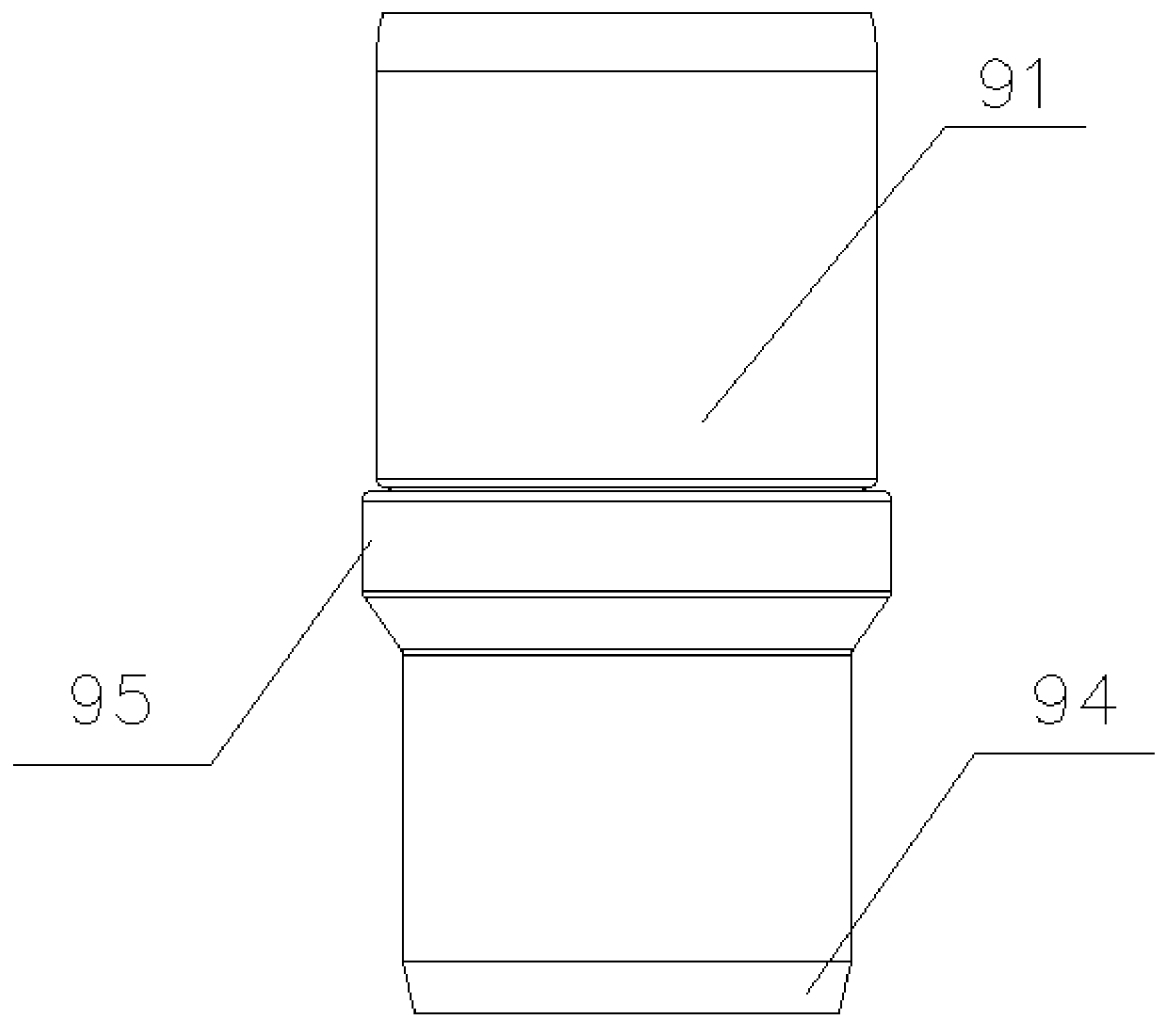
FIG. 22 is a structural view illustrating the loading ring that is mounted onto the transparent loading cap as illustrated in FIG. 19.

Referring to FIG. 18 or FIG. 22, the front end of the transparent loading cap 91 is further provided with a loading ring 94 made from hard metal material such as stainless steel or nickel-titanium alloy. Because a transparent loading cap 91 is usually made of PTFE, PC or PVC material and is softer than the anastomosis clamp 3, if the anastomosis clamp 3 is loaded onto or released from the transparent loading cap 91, the loading may be difficult or the releasing may fail due to the spinous part 3012 of the anastomosis clamp 3 piercing into the outer wall of the transparent loading cap 91. By providing the loading ring 94, it becomes relatively easy to mount the anastomosis clamp 3 onto the transparent loading cap 91. When the anastomosis clamp 3 is loaded onto the transparent loading cap 91, the front end of the anastomosis clamp 3 abuts against the outer wall of the loading ring 94. A certain pushing force is applied to the rear end of the anastomosis clamp 3, so that the anastomosis clamp 3 may be released relatively easily. During the process of releasing the anastomosis clamp 3, the anastomosis clamp 3 contacts the loading ring 94 with friction. The friction force between the anastomosis clamp 3 and the loading ring 94 made of hard metal material is relatively smaller in comparison with the friction force between the transparent loading cap 91 made from PC, PTFE or PVC material in the prior art and the anastomosis clamp 3, and thus the success rate for releasing the anastomosis clamp is greatly improved.

Figure 21:
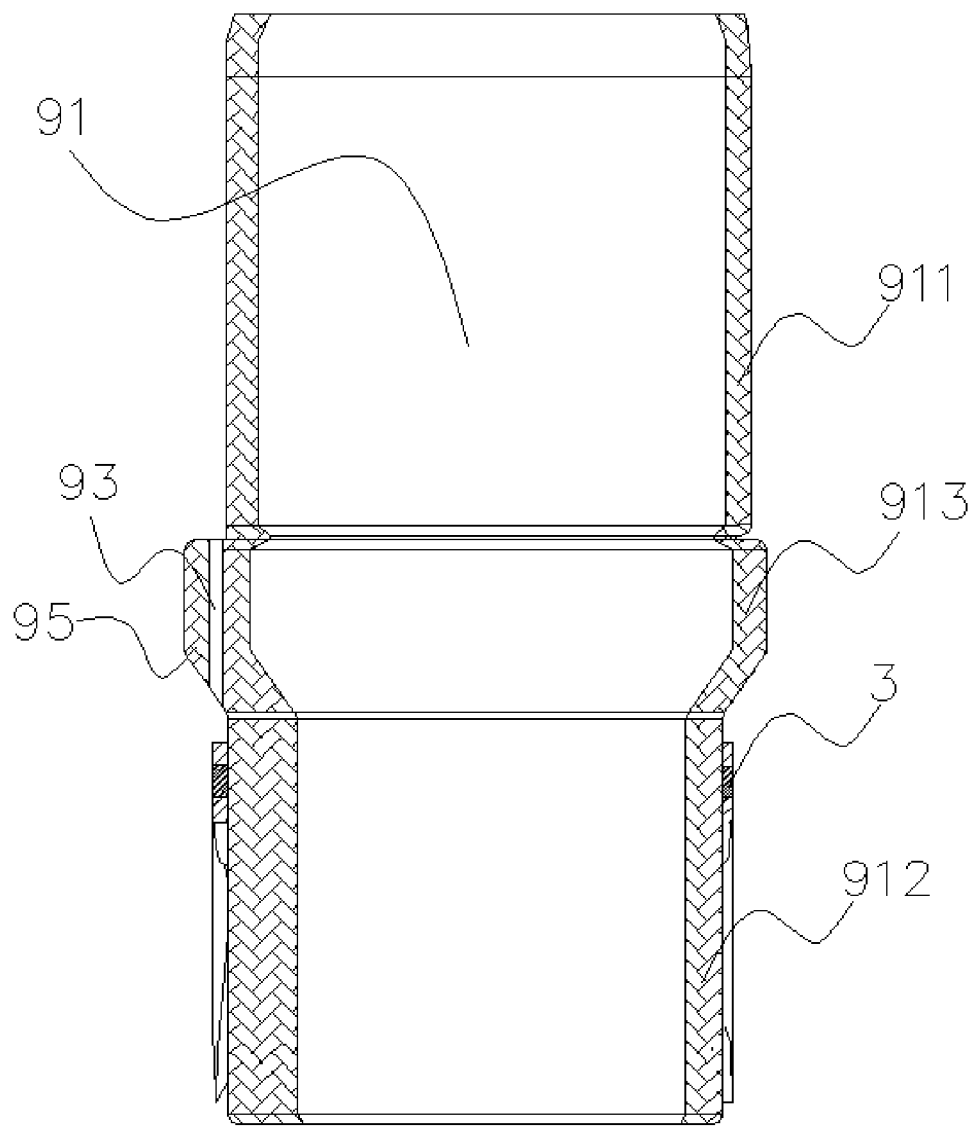
FIG. 21 is a sectional view illustrating a structure of the anastomosis clamp that is sleeved on the transparent loading cap according to an embodiment of the present disclosure.

Referring to FIG. 21, in the present embodiment, the spinous part 3012 of the anastomosis clamp 3 can abut against the outer wall of the loading ring 94. The anastomosis clamp 3 per se is made from nickel-titanium alloy, the spinous part 3012 can therefore slide on the outer surface of the loading ring 94 without being embedded into the loading ring 94.

According to another embodiment of the present disclosure, when the anastomosis clamp 3 is in a loaded state, the spinous part 3012 is opened by the loading ring 94 on the transparent loading cap 91. At this time, at least a portion of the spinous part 3012 abuts against the outer surface of the loading ring 94. When the anastomosis clamp 3 is released, portions of the spinous part 3012 of the anastomosis clamp 3 bend and close toward each other under a restoration force of its shape memory alloy material, so as to clamp the target tissue.

In the present embodiment, the transparent loading cap 91 includes a main body 911 and a loading ring 94. The main body 911 is penetrated therethrough along a central axis in the axial direction thereof and is made from transparent or semitransparent material. One end of the main body 911 is provided with a sleeve-connected segment 912 configured to be sleeved with the anastomosis clamp 3. The loading ring 94 is provided closer to a front end of the sleeve-connected segment 912, and is located at the outer side of the main body 911. The push hole 93 is located in rear of the sleeve-connected segment 912. The loading ring 94 being provided closer to the front end of the sleeve-connected segment 912 means that the loading ring 94 is at a small distance usually no more than 0.5 mm from the front end of the sleeve-connected segment 912, or the loading ring 94 is directly connected at the front end of the sleeve-connected segment 912. The spinous part 3012 can be detached from the transparent loading cap 91 in an instant moment after the spinous part 3012 is separated from the loading ring 94. Since the push hole 93 is provided in the wall of the transparent loading cap 91, and the push rod 92 needs to abut against the rear end of the anastomosis clamp 3 after passing through the push hole 93, an outer diameter of the transparent loading cap 91 at an end wall where the push hole 93 is located shall be greater than an outer diameter of the transparent loading cap 91 at an end wall (i.e., the sleeve-connected segment 912) where the anastomosis clamp 3 is located, so as to guarantee that the push rod 92 is located outside the transparent loading cap 91. As illustrated in FIG. 18 to FIG. 21, the main body 911 further includes a position-limiting segment 913 connected with the sleeve-connected segment 912. The position-limiting segment 913 has an outer diameter greater than that of the sleeve-connected segment 912, and the push hole 93 is located on the position-limiting segment 913. On one hand, the position-limiting segment 913 can increase the wall thickness of the transparent loading cap 91 to allow the passage of the push rod 92, and the transparent loading cap 91 has a reduced outer diameter in front and rear of the position-limiting segment 913. On the other hand, the position-limiting segment 913 can restrain the anastomosis clamp 3 from going beyond the sleeve-connected segment 912, so as to avoid axial movement of the anastomosis clamp 3 and to keep positional relation between the spinous part 3012 of the anastomosis clamp 3 and the loading ring 94.

In the present embodiment, in order to facilitate the anastomosis clamp 3 being released quickly, the loading ring 94 may be configured as a taper-shaped structure with an outer diameter gradually decreasing from the rear to the front.

The push rod 92 may be of but not limited to a following structure. As illustrated in FIG. 14 and FIG. 15, the push rod 92 includes a rod body 921 and a push handle 922 connected at an end of the rod body 921. The other end of the rod body 921 is configured to abut against the rear end of the anastomosis clamp 3. The rod body 921 is a straight rod, and the push handle 922 is configured to be operated by an operator manually. Since the push rod 92 is located outside, it would be in contact with the human skin tissue. In order to avoid damage to the skin tissue or contamination to the instrument, a rubber sheath 923 is provided around the out peripheral surface of the rod body 921. The rubber sheath 923 is made from medical silicone and is completely wrapped around the outer peripheral surface of the rod body 921.

As illustrated in FIG. 18, according to another embodiment of the present disclosure, the front end of the sleeve-connected segment 912 is provided with an oblique surface 9121, and the outer side of the sleeve-connected segment 912 that is in rear of the oblique surface 9121 is provided with a ring-shaped groove 9122 configured to hold the loading ring 94. The loading ring 94 has a width of 1 mm, the ring-shaped groove 9122 has a width slightly larger than 1 mm, and the width of the oblique surface 9121 (the size along the axial direction of the sleeve-connected segment 912) is 0.5 mm. In another embodiment not shown, the ring-shaped groove 9122 extends directly from the front end of the transparent loading cap 91 towards the rear end of the transparent loading cap 91. Therefore, by applying glue onto the front end of the transparent loading cap 91 or the inner wall of the loading ring 94, a fixed adhesion connection can be achieved by inserting the front end of the transparent loading cap 91 into the loading ring 94. Alternatively, the size of the outer diameter of the ring-shaped groove 9122 is set relatively larger and the size of the inner diameter of the loading ring 94 is set relatively smaller, in this way the ring-shaped groove 9122 and the loading ring 94 can be fixed with each other by snap-fit connection. The provision of the oblique surface 9121 makes a part of the sleeve-connected segment 912 in front of the loading ring 94 have a smaller diameter. At the instant moment when the anastomosis clamp 3 is detached from the sleeve-connected segment 912, the spinous part 3012 will not be embedded into the end of the sleeve-connected segment 912. The loading ring 94 may be adhered to the ring-shaped groove 9122 or be snap-fitted to the ring-shaped groove 9122 through interference fit. The provision of the oblique surface 9121 also facilitates mounting of the loading ring 94. In the present embodiment, in order to facilitate the quick release of the anastomosis clamp 3, the loading ring 94 may be provided as a taper-shaped structure with an outer diameter gradually decreasing from the rear to the front.

In the embodiment illustrated in FIG. 18, in the process of loading the anastomosis clamp 3, the oblique surface 9121 provides a guiding function, and avoids a large frictional resistance or scratch on the inner wall of the endoscope channel when the releasing assembly is assembled with the endoscope. The loading ring 94 is configured to be fixed to the ring-shaped groove 9122 via a snap-fit connection under the corporation of the ring-shaped groove 9122 with the rear end of the oblique surface 9121.

Figure 19:
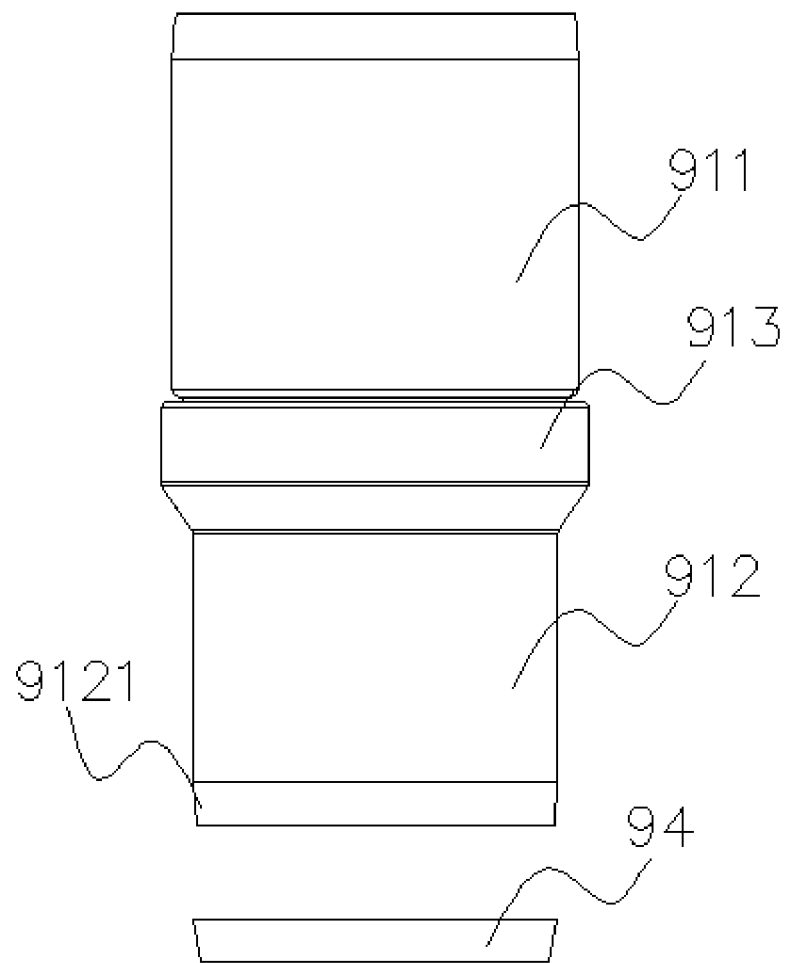
FIG. 19 is a exploded view illustrating a structure of a transparent loading cap and a loading ring according to another embodiment of the present disclosure.

As illustrated in FIG. 19, according to another embodiment of the present disclosure, in contrast with the embodiment illustrated in FIG. 18, the sleeve-connected segment 912 of the transparent loading cap 91 is not provided with the ring-shaped groove 9122, and the loading ring 94 is a taper-shaped cylinder structure rather than a straight cylinder structure, so as to be fitted with the oblique surface 9121. In the present embodiment, the loading ring 94 is fixed with the oblique surface 9121 of the transparent loading cap through adhesive dripping. In the present embodiment, the ring-shaped groove 9122 is eliminated, so that the manufacture process becomes relatively easier. The loading ring 94 and the front end of the sleeve-connected segment 912 are fixed with each other via oblique surfaces thereof which are adhered to each other through the adhesive dripping. After the assembling between the loading ring 94 and the transparent loading cap 91 is finished, during the process of sleeving the anastomosis clamp 3 on the oblique surface 9121 at the front end of the transparent loading cap 91, the spinous part 3012 would be inevitably in frictional contact with the oblique surface 9121 at the front end of the transparent loading cap 91, because the spinous part 3012 of the anastomosis clamp 3 in a natural (i.e., closed) state is facing toward the center of the anastomosis clamp 3 in the radial direction. In the present embodiment, since the oblique surface 9121 is adhered, at its outer side, with a loading ring 94 made from hard metal material, the frictional resistance can be greatly reduced and the assembling efficiency can be improved.

Additionally, throughout the specification of the present disclosure, unless otherwise indicated, "a plurality of" means two or more than two.

In the specification, the illustrative description of the terms does not necessarily represent the same embodiment, and the described specific feature, structure, material or characteristic may be combined in a proper manner in any one or more embodiments.

Based on the above description to the desired embodiments of the present disclosure and the above contents, a person in the related art may make various alterations and amendments to the above embodiments without departing from the scope of the technical idea of the present disclosure. The technical scope of the present disclosure is not limited to the above contents in the specification and shall be defined only by the claims.

What is claimed is:

1. A fetching assembly for an anastomosis clamp, comprising a fetching cap, a fetching hook and an anastomosis clamp, wherein the fetching cap is configured to be mounted on a front end of an endoscope, a front end of the fetching cap is configured to be accommodated in the anastomosis clamp, and the fetching hook is configured to pass through the fetching cap and to hook onto the anastomosis clamp, and when the fetching hook is pulled backward, the fetching hook drives the anastomosis clamp to be sleeved on an outer peripheral surface of the front end of the fetching cap.

2. The fetching assembly for the anastomosis clamp according to claim 1, wherein the anastomosis clamp comprises a clamp body and a fetching thread, a front end of the clamp body is closable, a rear end of the clamp body is provided with a plurality of threading holes along a circumferential direction thereof, and the fetching thread is configured to pass through the threading hole to be fixed to the clamp body.

3. The fetching assembly for the anastomosis clamp according to claim 2, wherein a plurality of fetching threads are provided and are connected with each other, and a connection point of the plurality of fetching threads is located on a central axis of the clamp body.

4. The fetching assembly for the anastomosis clamp according to claim 2, wherein the fetching cap comprises a fetching cap body and a fixer fixed at a rear end of the fetching cap body, the fixer is configured to be mounted at the front end of the endoscope, and a front end of the fetching cap body is provided with two or more slots.

5. The fetching assembly for the anastomosis clamp according to claim 4, wherein the front end of the fetching cap body is provided with an arc-shaped chamfer.

6. The fetching assembly for the anastomosis clamp according to claim 4, wherein two sides of each of the two or more slots are provided, at the front end of the fetching cap body, with a chamfered oblique surface.

7. The fetching assembly for the anastomosis clamp according to claim 1, wherein the fetching hook comprises a handle and a hook part located at a front end of the handle.

8. The fetching assembly for the anastomosis clamp according to claim 7, wherein the fetching hook further comprises a sliding ring and a pull rope, the sliding ring is slidably connected to the handle, the handle has an axial hole penetrating through the front end of the handle, and the pull rope has one end connected with the sliding ring and another end connected with the hook part.

9. A fetching assembly for an anastomosis clamp, the fetching assembly being configured to be used in cooperation with an endoscope and fetch the anastomosis clamp by use of the endoscope, the anastomosis clamp comprising a clamp body and a fetching thread, a front end of the clamp body being configured to be closed in a natural state, a rear end of the clamp body being provided with at least two threading holes along a circumferential direction thereof, and the fetching thread being configured to pass through the at least two threading holes to be fixed to the clamp body, wherein:

the fetching assembly comprises a fetching cap penetrated therethrough in a front-rear direction thereof and a fetching hook configured to move along an internal axis of the fetching cap in the front-rear direction, the fetching cap is configured to be mounted on a front end of the endoscope, a front end of the fetching cap is configured to be sleeved with the anastomosis clamp, the fetching hook is configured to pass through the fetching cap and hook onto the fetching thread, and when the fetching hook is pulled to drive the fetching thread to move backward, the fetching hook drives the anastomosis clamp to be sleeved on an outer peripheral surface of the front end of the fetching cap to allow the front end of the anastomosis clamp to be in an opened state.

10. The fetching assembly for the anastomosis clamp according to claim 9, wherein the fetching cap comprises a fetching cap body and a fixer fixed at a rear end of the fetching cap body, the fixer is configured to be mounted at the front end of the endoscope, and a front end of the fetching cap body is provided with two or more slots.

11. The fetching assembly for the anastomosis clamp according to claim 9, further comprising a handle, wherein the handle and the fetching hook are connected with each other in relatively fixed way.

12. The fetching assembly for the anastomosis clamp according to claim 11, wherein a front end of the fetching hook is provided with a hook part, the handle further comprises a sliding ring and a pull rope, the sliding ring is slidably connected to the handle, the handle has an axial hole penetrating through the front end of the handle, and the pull rope has one end connected with the sliding ring and another end connected with the hook part.

* * * * *